United States Patent
Fukushima et al.

(10) Patent No.: US 8,247,611 B2
(45) Date of Patent: Aug. 21, 2012

(54) PROCESS FOR PRODUCING NITROGEN-CONTAINING COMPOUNDS

(75) Inventors: Tetsuaki Fukushima, Wakayama (JP); Masaharu Jono, Wakayama (JP); Michio Terasaka, Wakayama (JP)

(73) Assignee: KAO Corporation, Tokyo (JP)

(*) Notice: Subject to any disclaimer, the term of this patent is extended or adjusted under 35 U.S.C. 154(b) by 585 days.

(21) Appl. No.: 12/159,526

(22) PCT Filed: Dec. 21, 2006

(86) PCT No.: PCT/JP2006/326164
§ 371 (c)(1),
(2), (4) Date: Nov. 12, 2009

(87) PCT Pub. No.: WO2007/077903
PCT Pub. Date: Jul. 12, 2007

(65) Prior Publication Data
US 2010/0274056 A1    Oct. 28, 2010

(30) Foreign Application Priority Data

Dec. 28, 2005 (JP) .................... 2005-379652
Dec. 28, 2005 (JP) .................... 2005-379655
Dec. 28, 2005 (JP) .................... 2005-379660

(51) Int. Cl.
*C07C 209/14* (2006.01)
*C07C 209/16* (2006.01)

(52) U.S. Cl. ........................ 564/479; 564/480

(58) Field of Classification Search ............... None
See application file for complete search history.

(56) References Cited

U.S. PATENT DOCUMENTS

| | | |
|---|---|---|
| 4,755,369 A | 7/1988 | Yoshiharu |
| 4,863,690 A | 9/1989 | Berthold et al. |
| 5,817,593 A | 10/1998 | Chang et al. |
| 5,908,607 A | 6/1999 | Abekawa et al. |
| 5,916,838 A | 6/1999 | Wulff-Doring et al. |
| 5,958,825 A | 9/1999 | Wulff-Doring et al. |
| 6,057,442 A * | 5/2000 | Wulff-Doring et al. ...... 544/106 |
| 2007/0149817 A1 | 6/2007 | Fukushima et al. |
| 2007/0276162 A1 | 11/2007 | Malek et al. |

FOREIGN PATENT DOCUMENTS

| | | |
|---|---|---|
| EP | 0 839 575 | 5/1998 |
| EP | 1 190 768 | 3/2002 |
| GB | 1 176 337 | 1/1970 |
| JP | 06 001758 | 1/1994 |
| JP | 8-243392 | 9/1996 |
| JP | 10-174875 | 6/1998 |
| JP | 2001-501524 | 2/2001 |
| JP | 2004-43319 | 2/2004 |
| JP | 2004-203875 | 7/2004 |
| WO | WO 2005/082834 A1 | 9/2005 |

OTHER PUBLICATIONS

Hu, Jian et al. "Study on Process for Synthesis of 2-ethylhexylamine by animation and dehydration of 2-ethylhexyl alcohol", Chemical Abstracts Service, vol. 20 No. 2 pp. 157-160 (2004), (English abstract only).

Elizarova, G.L. et al., "Synthesis of Cobaly (III), Manganese (III), Ruthenium (IV) Immobilized Hydroxides and Its Catalytic Properties In The Reaction of Water Oxidation", Chemical Abstracts Service, vol. 3 pp. 86-93, (1990), (English abstract only).

Office Action issued May 17, 2011, in Japanese Patent Application No. 2005-379652 (with English-language translation).

Office Action issued Jun. 14, 2011, in Japanese Patent Application No. 2005-379660 (with English-language translation).

Filipino Office Action mailed Oct. 13, 2011, in Patent Application No. 12008501518 (English translation only).

Office Action issued Apr. 1, 2011 in China Application No. 200680049449.0 (With English Translation).

Office Action issued Jan. 24, 2012, in Japanese Patent Application No. 2006-337204 (with English-language translation).

* cited by examiner

*Primary Examiner* — Brian J Davis
(74) *Attorney, Agent, or Firm* — Oblon, Spivak, McClelland, Maier & Neustadt, L.L.P.

(57) ABSTRACT

The present invention relates to a process for producing an aliphatic amine, comprising the step of contacting a linear or branched, or cyclic aliphatic alcohol having 6 to 22 carbon atoms with ammonia and hydrogen in the presence of a catalyst formed by supporting at least (A) a ruthenium component produced by hydrolysis of a ruthenium compound on a carrier, or by further supporting, in addition to the component (A), a specific second metal component or a specific third metal component on the carrier. According to the process of the present invention, an aliphatic primary amine can be produced from an aliphatic alcohol with a high catalytic activity and a high selectivity.

16 Claims, No Drawings

PROCESS FOR PRODUCING NITROGEN-CONTAINING COMPOUNDS

FIELD OF THE INVENTION

The present invention relates to a process for producing nitrogen-containing compounds, in particular, aliphatic amines.

BACKGROUND OF THE INVENTION

Aliphatic primary amines are important compounds in domestic and industrial application fields and have been used as raw materials for production of surfactants, fiber-treating agents, etc.

The aliphatic primary amines have been produced by various processes. As one of the production processes, there is known the method of contacting an aliphatic primary alcohol with ammonia and hydrogen in the presence of a catalyst. In the catalytic reaction, there has been used a nickel/copper-based catalyst or a noble metal-based catalyst.

As the methods using the noble metal-based catalyst, in particular, a ruthenium-based catalyst, there is disclosed, for example, the process for producing an amine from an alcohol, etc., in the presence of a catalyst formed by supporting about 0.001 to 25% by weight of ruthenium together with about 0 to 5% by weight of a co-catalyst such as rhodium, palladium, platinum, copper, silver and a mixture thereof, on a porous oxide such as alumina, silica and an aluminosilicate (e.g., refer to JP 8-243392A). Also, there are disclosed the process using a catalyst formed by supporting about 0.001 to 25% by weight of ruthenium and about 0.1 to 6% by weight of cobalt and/or nickel together with about 0 to 10% by weight of copper and about 0 to 5% by weight of an accelerator composed of various metals on a porous oxide such as alumina, silica and an aluminosilicate (e.g., refer to JP 10-174874A), and the process using a catalyst formed by supporting about 0.001 to 25% by weight of ruthenium and about 6 to 50% by weight of cobalt and/or nickel together with about 0 to 10% by weight of copper and about 0 to 5% by weight of an accelerator composed of various metals on a porous oxide such as alumina, silica and an aluminosilicate (e.g., refer to JP 10-174875A).

In these techniques, the catalysts are produced by an impregnating method, and the catalyst produced is dried, baked at 400° C. for 4 h, and then subjected to hydrogen reducing treatment at 300° C. for 20 h. Further, the catalysts fail to exhibit sufficient reactivity and selectivity.

SUMMARY OF THE INVENTION

The present invention relates to:

(1) A process for producing an aliphatic amine, including the step of contacting a linear or branched, or cyclic aliphatic alcohol having 6 to 22 carbon atoms with ammonia and hydrogen in the presence of a catalyst formed by supporting (A) a ruthenium component produced by hydrolysis of a ruthenium compound on a carrier;

(2) a process for producing an aliphatic amine, including the step of contacting a linear or branched, or cyclic aliphatic alcohol having 6 to 22 carbon atoms with ammonia and hydrogen in the presence of a catalyst, wherein the catalyst is formed by supporting (A) a ruthenium component and (B) at least one metal component selected from the group consisting of nickel, cobalt and tungsten which are respectively produced by hydrolysis of a ruthenium compound and a compound of at least one metal selected from the group consisting of nickel, cobalt and tungsten, on a carrier; and (3) a process for producing an aliphatic amine, including the step of contacting a linear or branched, or cyclic aliphatic alcohol having 6 to 22 carbon atoms with ammonia and hydrogen in the presence of a catalyst, wherein the catalyst is formed by supporting (A) a ruthenium component, (B') at least one metal component selected from the group consisting of nickel and cobalt and (C) at least one metal component selected from the group consisting of lanthanum, yttrium, magnesium and barium, on a carrier.

DETAILED DESCRIPTION OF THE INVENTION

The present invention relates to a process for producing an aliphatic amine, in particular, an aliphatic primary amine, from an aliphatic alcohol with a high catalytic activity and a high selectivity.

In the process for producing an aliphatic amine according to the present invention, as the raw material, there is used a linear or branched, or cyclic, saturated or unsaturated aliphatic alcohol having 6 to 22 carbon atoms.

Examples of the aliphatic alcohol usable in the present invention include hexyl alcohol, isohexyl alcohol, octyl alcohol, isooctyl alcohol, 2-ethylhexyl alcohol, nonyl alcohol, isononyl alcohol, 3,5,5-trimethylhexyl alcohol, decyl alcohol, 3,7-dimethyloctyl alcohol, 2-propylheptyl alcohol, dodecyl alcohols such as lauryl alcohol, tetradecyl alcohols such as myristyl alcohol, hexadecyl alcohols, octadecyl alcohols such as stearyl alcohol, oleyl alcohol, behenyl alcohol, icosyl alcohols, geraniol, cyclopentyl methanol, cyclopentenyl methanol, cyclohexyl methanol and cyclohexenyl methanol.

In the present invention, among the above aliphatic alcohols, preferred are linear aliphatic alcohols having 6 to 22 carbon atoms, and more preferred are linear aliphatic alcohols having 8 to 22 carbon atoms.

In the present invention, as the catalyst, there are used (1) a catalyst formed by supporting (A) a ruthenium component produced by hydrolysis of a ruthenium compound on a carrier; (2) a catalyst formed by supporting (A) a ruthenium component and (B) at least one metal component selected from the group consisting of nickel, cobalt and tungsten which are respectively produced by hydrolysis of a ruthenium compound and a compound of at least one metal selected from the group consisting of nickel, cobalt and tungsten, on a carrier (hereinafter referred to merely as a "second metal component (B)"); or (3) a catalyst formed by supporting (A) a ruthenium component, (B') at least one metal component selected from the group consisting of nickel and cobalt (hereinafter referred to merely as a "second metal component (B)'"; and (C) at least one metal component selected from the group consisting of lanthanum, yttrium, magnesium and barium (hereinafter referred to merely as a "third metal component (C)"), on a carrier (hereinafter, the above catalysts (1) to (3) are occasionally totally referred to merely as a "ruthenium-based catalyst"). In each of above catalysts (1) to (3), examples of the carrier include a high molecular compound, a metal phosphate, and a porous oxide. Examples of the porous oxide used in the present invention include alumina, zirconia, titania, silica, activated carbon, aluminosilicates, diatomaceous earth, hydrotalcite-type compounds such as, for example, a magnesium/aluminum-based composite oxide, alkali earth metal oxides, and, niobia. Examples of the high molecular compound include polystyrene, nylon and chelate resin, and examples of the metal phosphate include calcium phosphate and aluminum calcium phosphate. Among these carriers, in view of a high catalytic activity and a high selectivity, preferred is porous oxide, more preferred are alumina, zirconia, titania and aluminosilicates, and even more preferred are alumina and zirconia. In particular, the catalysts produced by using zirconia or titania exhibit a higher catalytic activity, whereas the catalysts produced by using alumina or an aluminosilicate exhibit a higher selectivity to primary amines.

In the present invention, the carriers such as high molecular compound, a metal phosphate, a porous oxide may be used alone or in combination of any two or more thereof.

The ruthenium-based catalyst used in the present invention is formed by supporting the ruthenium component (A) solely, both of the ruthenium component (A) and the second metal component (B), or all of the ruthenium component (A), the second component (B') and the third metal component (C), on the above carrier. In the above catalyst (1), the ruthenium component (A) is supported on the carrier by hydrolyzing a ruthenium compound. In the above catalyst (2), the ruthenium component (A) and the second metal component (B) are supported on the carrier by hydrolyzing the ruthenium compound and a compound of at least one metal selected from the group consisting of nickel, cobalt and tungsten, respectively. In the above catalyst (3), the ruthenium component (A), the second metal component (B') and the third metal component (C) are supported on the carrier by hydrolyzing the ruthenium compound, a compound of at least one metal selected from the group consisting of nickel and cobalt, and a compound of at least one metal selected from the group consisting of lanthanum, yttrium, magnesium and barium, respectively.

The method of supporting these components is not particularly limited, and includes any optional conventionally known method such as impregnation method, precipitation method, ion exchange method and kneading method.

As the second metal component (B) to be supported on the carrier, in view of improving a catalytic activity and a selectivity of the resultant catalyst, there is used a metal component selected from the group consisting of nickel, cobalt and tungsten. These second metal components may be supported alone or in combination of any two or more thereof. As the second metal component (B') to be supported on the carrier, in view of improving a catalytic activity and a selectivity of the resultant catalyst, there is used at least one metal component selected from the group consisting of nickel and cobalt. Among these second metal components (B'), preferred is a nickel component. Also, as the third metal component (C) to be supported on the carrier, in view of obtaining a catalyst having both a high catalytic activity and a high selectivity, there is used at least one metal component selected from the group consisting of lanthanum, yttrium, magnesium and barium and preferably at least one metal component selected from the group consisting of lanthanum and magnesium.

Next, the process for producing the respective ruthenium-based catalysts is illustratively explained.

First, the above catalyst (1) may be produced by adding the carrier such as porous oxide to a medium such as ion-exchanged water to prepare a suspension, and then adding a solution prepared by dissolving the ruthenium compound in an aqueous medium such as ion-exchanged water to the suspension, if required, followed by heating while stirring to control a temperature of the suspension to about 20 to 95° C. and preferably 40 to 80° C. The above catalyst (2) and the above catalyst (3) may be produced in the same manner as used for production of the catalyst (1) except for using a solution prepared by dissolving a ruthenium compound as a source of the ruthenium component (A) and a metal compound as a source of the second metal component (B) in an aqueous medium, and a solution prepared by dissolving the ruthenium compound, a metal compound as a source of the second metal component (B') and a metal compound as a source of the third metal component (C) in an aqueous medium, respectively.

Examples of the ruthenium compound include chlorides, nitrates, formates, ammonium salts, etc., of ruthenium. Examples of the metal compound as a source of the second metal component (B) or (B') and the metal compound as a source of the third metal component (C) include chlorides, nitrates, carbonates, sulfates, ammonium salts, etc., of the respective components.

Next, an alkali is added to a suspension containing the respective compounds as sources of the respective metal components to adjust a pH of the suspension to about 4 to 12 and preferably about 6 to 11, thereby allowing the respective compounds to be hydrolyzed. Then, the obtained reaction mixture was aged to support the respective components on the carrier such as the porous oxide. The alkali is not particularly limited. Examples of the alkali usable in the present invention include aqueous ammonia, and carbonates, hydroxides, etc., of an alkali metal such as sodium and potassium. The temperature and time required from the adjustment of pH to the aging is not particularly limited as long as a sufficient hydrolysis of the ruthenium compound is ensured.

Next, the reaction mixture is subjected to reducing treatment by adding a reducing agent such as, for example, formaldehyde, hydrazine and sodium borohydride thereto and, if required, heating the mixture to about 20 to 95° C. and preferably 60 to 95° C. Thereafter, the obtained reaction solution is subjected to solid-liquid separation such as filtration to obtain solids. The thus obtained solids are fully washed with water and then dried at a temperature of preferably 140° C. or lower under normal pressure or reduced pressure. These reducing agents may be used alone or in combination of any two or more thereof.

The reducing agent may be used in an amount of usually about 1 to 50 mol and preferably 15 to 40 mol per one mol of the whole metal components supported in order to effectively reduce the respective metal components supported.

The reducing treatment time is not particularly limited as long as the time for allowing the reduction reaction to proceed to a desirable extent is ensured.

Meanwhile, the above reducing treatment is not essential. After supporting the respective components on the carrier by hydrolysis, the solids obtained by the solid-liquid separation procedure may be fully washed with water and then dried.

In the present invention, the above water-washing procedure is preferably conducted to such an extent that the obtained filtrate has an electric conductivity of 50 µS/cm or less, in order to prevent counter ions from remaining in the resultant catalyst.

In the present invention, when the respective metal components are supported on the carrier by the above hydrolysis method, the procedures such as high-temperature baking treatment usually required for impregnation method, etc., and high-temperature reducing treatment under an inert gas atmosphere, are not necessarily needed, resulting in a simple procedure for production of the catalyst.

The thus produced ruthenium-based catalyst preferably contains the ruthenium component (A) in an amount of about 0.1 to 25% by mass and more preferably 1 to 15% by mass in terms of metallic ruthenium on the basis of a total amount of the catalyst including the carrier in view of sufficient catalytic activity and selectivity and low costs. Also, the ruthenium-based catalyst preferably contains the second metal component (B) or (B') in an amount of about 0.1 to 25% by mass and more preferably 0.2 to 15% by mass in terms of the metal element on the basis of a total amount of the catalyst including the carrier. Further, the ruthenium-based catalyst preferably contains the third metal component (C) in an amount of about 0.01 to 10% by mass and more preferably 0.05 to 5% by mass in terms of the metal element on the basis of a total amount of the catalyst including the carrier.

The content of the ruthenium component (A) in the catalyst may be measured by ICP emission spectral analysis after melting the catalyst using ammonium hydrogen sulfate. The contents of the second metal component (B) or (B') and the third metal component (C) may also be measured by ICP emission spectral analysis after subjecting the catalyst to wet decomposition treatment (using sulfuric acid/hydrogen peroxide) in the case where the carrier contains no silicon, or after subjecting the catalyst to an alkali melting treatment in the case where the carrier contains silicon.

In the process for producing an aliphatic amine according to the present invention, the aliphatic alcohol as the raw material is contacted with ammonia and hydrogen in the presence of the thus produced ruthenium-based catalyst to produce an aliphatic amine and preferably an aliphatic primary amine.

The catalytic reaction may be carried out in either a batch type closed system or a batch type flow system, or in a fixed bed flow system. The amount of the catalyst used varies depending upon the kind of reaction system used. In a batch type reaction system, in view of attaining good reactivity and selectivity, the catalyst is used in an amount of preferably 0.1 to 20% by mass and more preferably 0.5 to 10% by mass on the basis of the raw aliphatic alcohol. Also, in view of good conversion and selectivity and prevention of deactivation of the catalyst, the reaction temperature is from 120 to 280° C. and preferably from 180 to 250° C., and the reaction pressure is from normal pressure to 40 MPaG and preferably from 0.5 to 30 MPaG.

The molar ratio of ammonia to the aliphatic alcohol as the raw materials (ammonia/aliphatic alcohol) is usually from 0.5 to 10 and preferably from 2 to 7 in view of good conversion and good selectivity to primary amines. Ammonia may be added separately from hydrogen, or may be introduced in the form of a mixed gas of ammonia and hydrogen.

The molar ratio of hydrogen to the aliphatic alcohol as initial charges (hydrogen/aliphatic alcohol) is preferably from 0.01 to 3.0 and more preferably from 0.02 to 2.0 when used in a batch type closed system. When used in a batch type flow system or a fixed bed flow system, the molar ratio of hydrogen initially flowing through the system to the aliphatic alcohol is preferably from 0.01 to 1.0 and more preferably from 0.02 to 0.8. However, in any of the above reaction methods, the molar ratios in the course of the respective reactions are not necessarily limited to the above-specified ranges.

According to the production process of the present invention, an aliphatic amine, in particular, an aliphatic primary amine, can be produced from an aliphatic alcohol with a high catalytic activity and a high selectivity.

The present invention is described in more detail by referring to the following examples. However, it should be noted that these examples are only illustrative and not intended to limit the invention thereto.

Preparation Example 1

A separable flask was charged with 10.0 g of an alumina powder "A-11" available from Sumitomo Chemical Corp., and 170 g of ion-exchanged water to prepare a suspension, and then a solution prepared by dissolving 0.59 g of ruthenium chloride hydrate having a molecular weight of 252.68 in 40 g of ion-exchanged water was added thereto, followed by heating the suspension to 60° C. while stirring. The thus obtained suspension (at 60° C.) was stirred for 3 h, and then aqueous ammonia as a precipitant was dropped therein to adjust a pH of the suspension to 11 for hydrolysis thereof, followed by aging the suspension at 60° C. for 2 h. Then, the suspension was mixed with 4.8 g of a 37% by mass formalin solution and heated to 90° C. at which the suspension was reduced for 1 h. Thereafter, the obtained powder was separated by filtration, washed with ion-exchanged water until an electric conductivity of the filtrate reached 30 μs/cm or less, and then dried at 60° C. under a pressure of 13 kPa, thereby obtaining about 10 g of a 2% by mass ruthenium/alumina catalyst A.

Preparation Example 2

The same procedure as in Preparation Example 1 was repeated except for using 1.47 g of ruthenium chloride hydrate, thereby obtaining about 10 g of a 5% by mass ruthenium/alumina catalyst B.

Preparation Example 3

The same procedure as in Preparation Example 1 was repeated except for using a zirconia powder "RC-100" available from Dai-Ichi Kigenso Kagaku Kogyo Co., Ltd., in place of the alumina powder, thereby obtaining about 10 g of a 2% by mass ruthenium/zirconia catalyst C.

Preparation Example 4

The same procedure as in Preparation Example 1 was repeated except for using a titania powder "SSP-25" available from Sakai Kagaku Kogyo Co., Ltd., in place of the alumina powder, thereby obtaining about 10 g of a 2% by mass ruthenium/titania catalyst D.

Preparation Example 5

The same procedure as in Preparation Example 2 was repeated except for using a synthetic zeolite powder "CP814E" available from Zeolyst Inc., in place of the alumina powder, thereby obtaining about 10 g of a 5% by mass ruthenium/zeolite catalyst E.

Comparative Preparation Example 1

On a ceramic dish, 0.26 g of ruthenium trichloride was dissolved in 5.8 g of ion-exchanged water, and 6 g of an alumina powder "A-11" available from Sumitomo Chemical Corp., was immersed in the obtained solution, and allowed to stand at room temperature for 2 h. Next, the resultant suspension was heated to 65° C. and dehydrated while mixing, and then dried at 120° C. under normal pressure over whole day and night. The obtained dried powder was heated to 400° C. at a temperature rise rate of 5° C./min under an air flow fed at a rate of 3 Nm$^3$/h, and baked at 400° C. for 4 h, thereby obtaining about 6 g of a 2% by mass ruthenium/alumina catalyst F.

Example 1

A 500 mL autoclave of an electromagnetic induction rotary agitation type was charged with 150 g (0.55 mol) of stearyl alcohol and 3 g of the catalyst A produced in Preparation Example 1 (2.0% by mass on the basis of the raw alcohol), and then 47 g (2.76 mol) of ammonia was charged into the autoclave and further 0.17 mol of hydrogen was introduced under pressure thereinto such that a whole pressure in the autoclave as measured at room temperature reached 2.8 MPaG. Next, the contents of the autoclave were heated to a reaction temperature of 220° C. while stirring (at 1000 rpm). The initial maximum pressure in the autoclave at 220° C. was 16 MPaG. While continuously supplying hydrogen into the autoclave such that a whole pressure therein was maintained at a constant pressure of 16 MPaG, the contents of the autoclave were reacted with each other. The resultant reaction product was filtered to remove the catalyst therefrom, and then subjected to gas chromatography to analyze a composition thereof, thereby determining a conversion of the raw alcohol, a selectivity to stearyl amine, and an amount of by-products produced. The "conversion of alcohol" used herein means amount of alcohol consumed during reaction to amount of initial raw alcohol, whereas the "selectivity to stearyl amine" means amount of stearyl amine as a reaction product to amount of alcohol consumed during reaction (this definition is similarly applied to subsequent descriptions). The results are shown in Table 1.

Examples 2 to 5

The same procedure as in Example 1 was repeated except for using the catalysts (B), (C), (D) and (E) produced in Preparation Examples 2, 3, 4 and 5, respectively, in place of the catalyst (A), and supplying an additional amount of hydrogen such that the initial maximum pressure as measured at a reaction temperature of 220° C. was maintained at a constant value shown in Table 1. The resultant reaction products were analyzed in the same manner as in Example 1. The results are shown in Table 1.

TABLE 1

|  | Catalyst | Initial maximum pressure (MPaG) | Reaction time (h) |
| --- | --- | --- | --- |
| Example 1 | A | 16 | 6.0 |
| Example 2 | B | 16 | 6.0 |
| Example 3 | C | 16 | 6.0 |
| Example 4 | D | 16 | 6.0 |
| Example 5 | E | 16 | 4.0 |

|  | Conversion of raw alcohol (%) | Selectivity to stearyl amine (%) | Products (%) | |
| --- | --- | --- | --- | --- |
|  |  |  | Distearyl amine | Others |
| Example 1 | 86.3 | 85.5 | 5.9 | 6.6 |
| Example 2 | 96.4 | 75.0 | 10.3 | 13.8 |
| Example 3 | 94.0 | 76.2 | 11.1 | 11.3 |
| Example 4 | 91.2 | 76.6 | 10.9 | 10.4 |
| Example 5 | 93.2 | 81.2 | 8.8 | 8.7 |

Comparative Example 1

The same procedure as in Example 1 was repeated except for using the catalyst (F) produced in Comparative Preparation Example 1 in place of the catalyst (A). More specifically, the reaction was conducted for 6 h under the condition that the initial maximum pressure as measured at 220° C. was 16 MPaG. The resultant reaction product was analyzed in the same manner as in Example 1. As a result, it was confirmed that the conversion of the raw alcohol was 54.9%.

Example 6

The same procedure as in Example 3 was repeated except for using 150 g (0.81 mol) of lauryl alcohol in place of stearyl alcohol and using ammonia in an amount of 69 g (4.06 mol), thereby conducting the reaction for 11 h. The initial maximum pressure as measured at a reaction temperature of 220° C. was 21 MPaG. The resultant reaction product was analyzed in the same manner as in Example 1. As a result, it was confirmed that the conversion of the raw alcohol was 96.3%, the selectivity to lauryl amine was 74.9%, the amount of dilauryl amine produced is 12.3%, and the amount of the other by-products produced was 10.9%.

Preparation Example 6

A separable flask was charged with 10.0 g of a zirconia powder "RC-100" available from Dai-Ichi Kigenso Kagaku Kogyo Co., Ltd., and 170 g of ion-exchanged water to prepare a suspension, and then a solution prepared by dissolving 0.59 g of ruthenium chloride hydrate having a molecular weight of 252.68 and 0.18 g of nickel sulfate hexahydrate in 40 g of ion-exchanged water was added thereto, followed by heating the suspension to 60° C. while stirring. The thus obtained suspension (at 60° C.) was stirred for 10 h, and then an aqueous sodium carbonate solution as a precipitant was dropped therein to adjust a pH of the suspension to 11 for hydrolysis thereof, followed by aging the suspension at 60° C. for 2 h. Then, the suspension was mixed with 4.8 g of a 37% by mass formalin solution and heated to 90° C. at which the suspension was reduced for 1 h. Thereafter, the obtained powder was separated by filtration, washed with ion-exchanged water until an electric conductivity of the filtrate reached 30 μs/cm or less, and then dried at 60° C. under a pressure of 13 kPa, thereby obtaining about 10 g of a zirconia-supported 2% by mass ruthenium/0.4% by mass nickel catalyst G.

Preparation Example 7

The same procedure as in Preparation. Example 6 was repeated except for using 0.59 g of ruthenium chloride hydrate and 0.16 g of cobalt chloride hexahydrate, and using aqueous ammonia as a precipitant, thereby obtaining about 10 g of a zirconia-supported 2% by mass ruthenium/0.4% by mass cobalt catalyst H.

Preparation Example 8

A separable flask was charged with 10.0 g of a zirconia powder "RC-100" available from Dai-Ichi Kigenso Kagaku Kogyo Co., Ltd., and 170 g of ion-exchanged water to prepare a suspension, and then a solution prepared by dissolving 0.59 g of ruthenium chloride hydrate having a molecular weight of 252.68 in 40 g of ion-exchanged water was added thereto, followed by heating the suspension to 60° C. while stirring. The thus obtained suspension (at 60° C.) was stirred for 10 h, and then a solution prepared by dissolving 0.64 g of ammonium metatungstate in 20 g of ion-exchanged water, and aqueous ammonia were dropped therein to adjust a pH of the suspension to 11 for hydrolysis thereof, followed by aging the suspension at 60° C. for 2 h. Then, the suspension was mixed with 4.8 g of a 37% by mass formalin solution and heated to 90° C. at which the suspension was reduced for 1 h. Thereafter, the obtained powder was separated by filtration, washed with ion-exchanged water until an electric conductivity of the filtrate reached 30 μs/cm or less, and then dried at 60° C.

under a pressure of 13 kPa, thereby obtaining about 10 g of a zirconia-supported 2% by mass ruthenium/0.4% by mass tungsten catalyst I.

Preparation Example 9

A separable flask was charged with 10.0 g of a zirconia powder "RC-100" available from Dai-Ichi Kigenso Kagaku Kogyo Co., Ltd., and 170 g of ion-exchanged water to prepare a suspension, and then a solution prepared by dissolving 0.29 g of ruthenium chloride hydrate having a molecular weight of 252.68 and 0.72 g of nickel sulfate hexahydrate in 40 g of ion-exchanged water was added thereto, followed by heating the suspension to 60° C. while stirring. The thus obtained suspension (at 60° C.) was stirred for 10 h, and then aqueous ammonia as a precipitant was dropped therein to adjust a pH of the suspension to 11 for hydrolysis thereof, followed by aging the suspension at 60° C. for 2 h. Then, the suspension was mixed with 3.2 g of a 37% by mass formalin solution and heated to 90° C. at which the suspension was reduced for 1 h. Thereafter, the obtained powder was separated by filtration, washed with ion-exchanged water until an electric conductivity of the filtrate reached 30 μs/cm or less, and then dried at 120° C. under normal pressure, thereby obtaining about 10 g of a zirconia-supported 1% by mass ruthenium/1.6% by mass nickel catalyst J.

Preparation Example 10

The same procedure as in Preparation Example 6 was repeated except for using 10.0 g of an alumina powder "A-11" available from Sumitomo Chemical Corp., thereby obtaining about 10 g of an alumina-supported 2% by mass ruthenium/0.4% by mass nickel catalyst K.

Preparation Example 11

A separable flask was charged with 10.0 g of a zirconia powder "RC-100" available from Dai-Ichi Kigenso Kagaku Kogyo Co., Ltd., and 170 g of ion-exchanged water to prepare a suspension, and then a solution prepared by dissolving 0.29 g of ruthenium chloride hydrate having a molecular weight of 252.68 and 0.72 g of nickel sulfate hexahydrate in 40 g of ion-exchanged water was added thereto, followed by heating the suspension to 60° C. while stirring. The thus obtained suspension (at 60° C.) was stirred for 10 h, and then a 10% sodium hydroxide aqueous solution as a precipitant was dropped therein to adjust a pH of the suspension to 11 for hydrolysis thereof, followed by aging the suspension at 60° C. for 2 h. Then, after cooling, the obtained powder was separated by filtration, washed with ion-exchanged water until an electric conductivity of the filtrate reached 30 μs/cm or less, and then dried at 120° C. under normal pressure, thereby obtaining about 10 g of a zirconia-supported 1% by mass ruthenium/1.6% by mass nickel catalyst L.

Comparative Preparation Example 2

On a ceramic dish, 0.26 g of ruthenium trichloride was dissolved in 7.5 g of ion-exchanged water, and then 6 g of a zirconia powder "RC-100" available from Dai-Ichi Kigenso Kagaku Kogyo Co., Ltd., was immersed in the obtained solution, and allowed to stand at room temperature for 2 h. Then, the resultant suspension was heated to 65° C. and dehydrated while mixing, and then dried at 120° C. under normal pressure over whole day and night. The obtained dried powder was heated to 400° C. at a temperature rise rate of 5° C./min under an air flow fed at a rate of 3 Nm³/h, and baked at 400° C. for 4 h. Next, the thus obtained ruthenium-supporting zirconia powder was immersed in a solution prepared by dissolving 0.12 g of nickel nitrate hexahydrate in 7.4 g of ion-exchanged water, and then allowed to stand at room temperature for 2 h. Then, the resultant suspension was heated to 65° C. and dehydrated while mixing, and then dried at 120° C. under normal pressure over whole day and night. The obtained dried powder was heated to 400° C. at a temperature rise rate of 5° C./min under an air flow fed at a rate of 3 Nm³/h, and baked at 400° C. for 4 h, thereby obtaining about 6 g of a zirconia-supported 2% by mass ruthenium/0.4% by mass nickel catalyst M.

Example 7

A 500 mL autoclave of an electromagnetic induction rotary agitation type was charged with 150 g (0.55 mol) of stearyl alcohol and 3 g of the catalyst G produced in Preparation Example 6 (2.0% by mass on the basis of the raw alcohol), and then 47 g (2.76 mol) of ammonia was charged into the autoclave and further 0.17 mol of hydrogen was introduced under pressure thereinto such that a whole pressure in the autoclave as measured at room temperature reached 2.3 MPaG. Next, the contents of the autoclave were heated to a reaction temperature of 220° C. while stirring (at 1000 rpm). The initial maximum pressure in the autoclave at 220° C. was 16 MPaG. While continuously supplying hydrogen into the autoclave such that a whole pressure therein was maintained at a constant pressure of 16 MPaG, the contents of the autoclave were reacted with each other. The resultant reaction product was filtered to remove the catalyst therefrom, and then subjected to gas chromatography to analyze a composition thereof. The results are shown in Table 2.

Examples 8 and 9

The same procedure as in Example 7 was repeated except for using the catalysts (H) and (I) produced in Preparation Examples 7 and 8, respectively, in place of the catalyst (G), and supplying an additional amount of hydrogen such that the initial maximum pressure as measured at a reaction temperature of 220° C. was maintained at a constant value shown in Table 2. The resultant reaction products were analyzed in the same manner as in Example 7. The results are shown in Table 2.

Example 10

The same procedure as in Example 7 was repeated except for charging 6 g of the catalyst (J) produced in Preparation Example 9 (4.0% by mass on the basis of the raw alcohol) in place of the catalyst (G), and supplying an additional amount of hydrogen such that the initial maximum pressure as measured at a reaction temperature of 220° C. was maintained at a constant value shown in Table 2. The resultant reaction product was analyzed in the same manner as in Example 7. The results are shown in Table 2.

Example 11

The same procedure as in Example 7 was repeated except for charging 3 g of the catalyst (L) produced in Preparation Example 11 (2.0% by mass on the basis of the raw alcohol) in place of the catalyst (G), and supplying an additional amount of hydrogen such that the initial maximum pressure as measured at a reaction temperature of 220° C. was maintained at a constant value shown in Table 2. The resultant reaction product was analyzed in the same manner as in Example 7. The results are shown in Table 2.

TABLE 2

| | Catalyst | Initial maximum pressure (MPaG) | Reaction time (h) |
|---|---|---|---|
| Example 7 | G | 16 | 6.0 |
| Example 8 | H | 16 | 6.0 |
| Example 9 | I | 16 | 6.0 |
| Example 10 | J | 15 | 4.0 |
| Example 11 | L | 16 | 4.0 |

| | Conversion of raw alcohol (%) | Selectivity to stearyl amine (%) | Products (%) | |
|---|---|---|---|---|
| | | | Distearyl amine | Others |
| Example 7 | 97.0 | 87.6 | 9.1 | 2.9 |
| Example 8 | 97.3 | 78.7 | 15.8 | 4.9 |
| Example 9 | 96.5 | 70.6 | 19.3 | 9.1 |
| Example 10 | 98.1 | 90.3 | 7.2 | 2.3 |
| Example 11 | 97.6 | 89.0 | 9.6 | 1.1 |

Comparative Example 2

The same procedure as in Example 7 was repeated except for using the catalyst (M) produced in Comparative Preparation Example 2 in place of the catalyst (G). The reaction was conducted for 6 h, and the initial maximum pressure as measured at a reaction temperature of 220° C. was 16 MPaG. The resultant reaction product was analyzed in the same manner as in Example 7. As a result, it was confirmed that the conversion of the raw alcohol was 12.7%.

Example 12

The same procedure as in Example 7 was repeated except for using 150 g (0.81 mol) of lauryl alcohol in place of stearyl alcohol and using ammonia in an amount of 69 g (4.06 mol), thereby conducting the reaction for 9 h. The initial maximum pressure as measured at a reaction temperature of 220° C. was 21 MPaG. The resultant reaction product was analyzed in the same manner as in Example 7. As a result, it was confirmed that the conversion of the raw alcohol was 97.9%, the selectivity to lauryl amine was 90.4%, the amount of dilauryl amine produced is 8.9%, and the amount of the other by-products produced was 0.6%.

Example 13

A 500 mL autoclave of an electromagnetic induction rotary agitation type was charged with 150 g (0.55 mol) of stearyl alcohol and 3 g of the catalyst (G) produced in Preparation Example 6 (2.0% by mass on the basis of the raw alcohol), and then the contents of the autoclave were heated to 220° C. in a hydrogen atmosphere (0 MPaG) while stirring (at 1000 rpm). Then, while flowing ammonia and hydrogen through the autoclave at rates of 19.1 g (1.1 mol)/h and 2.6 L (0.12 mol)/h, respectively, so as to maintain the reaction pressure at a constant value of 2.0 MPaG, the reaction was conducted for 3 h. The resultant reaction product was filtered to remove the catalyst therefrom, and then subjected to gas chromatography to analyze a composition thereof. As a result, it was confirmed that the conversion of the raw alcohol was 96.0%, the selectivity to lauryl amine was 78.1%, the amount of dilauryl amine produced is 13.4%, and the amount of the other by-products produced was 7.6%.

Example 14

The same procedure as in Example 13 was repeated except for using the catalyst (K) produced in Preparation Example 10 in place of the catalyst (G), flowing ammonia and hydrogen through the autoclave at rates of 13.1 g (0.77 mol)/h and 4.3 L (0.19 mol)/h, respectively, thereby conducting the reaction for 6 h. The resultant reaction product was analyzed in the same manner as in Example 7. As a result, it was confirmed that the conversion of the raw alcohol was 65.5%, the selectivity to lauryl amine was 85.5%, the amount of dilauryl amine produced is 7.3%, and the amount of the other by-products produced was 2.2%.

Preparation Example 12

A separable flask was charged with 10.0 g of a zirconia powder "RC-100" available from Dai-Ichi Kigenso Kagaku Kogyo Co., Ltd., and 170 g of ion-exchanged water to prepare a suspension, and then a solution prepared by dissolving 0.29 g of ruthenium chloride hydrate having a molecular weight of 252.68, 0.72 g of nickel sulfate hexahydrate and 0.04 g of lanthanum nitrate in 40 g of ion-exchanged water was added thereto, followed by heating the suspension to 60° C. while stirring. The thus obtained suspension (at 60° C.) was stirred for 10 h, and then aqueous ammonia as a precipitant was dropped therein to adjust a pH of the suspension to 11 for hydrolysis thereof, followed by aging the suspension at 60° C. for 2 h. Then, the suspension was mixed with 3.2 g of a 37% by mass formalin solution and heated to 90° C. at which the suspension was reduced for 1 h. Thereafter, the obtained powder was separated by filtration, washed with ion-exchanged water until an electric conductivity of the filtrate reached 30 μs/cm or less, and then dried at 60° C. under a pressure of 13 kPa, thereby obtaining about 10 g of a zirconia-supported 1% by mass ruthenium/1.6% by mass nickel/0.1% by mass lanthanum catalyst N.

Preparation Example 13

The same procedure as in Preparation Example 12 was repeated except for using 0.29 g of ruthenium chloride hydrate, 0.72 g of nickel sulfate hexahydrate and 0.04 g of magnesium chloride, thereby obtaining about 10 g of a zirconia-supported 1% by mass ruthenium/1.6% by mass nickel/0.1% by weight magnesium catalyst O.

Preparation Example 14

The same procedure as in Preparation Example 12 was repeated except for using 0.29 g of ruthenium chloride hydrate, 0.72 g of nickel sulfate hexahydrate and 0.04 g of yttrium nitrate, thereby obtaining about 10 g of a zirconia-supported 1% by mass ruthenium/1.6% by mass nickel/0.1% by weight yttrium catalyst P.

Preparation Example 15

The same procedure as in Preparation Example 12 was repeated except for using 0.29 g of ruthenium chloride hydrate, 0.72 g of nickel sulfate hexahydrate and 0.02 g of barium nitrate, thereby obtaining about 10 g of a zirconia-supported 1% by mass ruthenium/1.6% by mass nickel/0.1% by weight barium catalyst Q.

Meanwhile, in the above Preparation Examples and Comparative Preparation Examples, the contents of the components (A), (B), (B') and (C) in the respective catalysts on the basis of a total amount of the catalyst were determined by the following ICP emission spectral analysis.

Measurement of Contents of Respective Components:

The content of the ruthenium component was measured as follows. That is, ammonium hydrogen sulfate was added to a sample (catalyst) such that ammonium hydrogen sulfate was used in an amount several tens times that of the catalyst sample, and the obtained mixture was melted under heating. The resultant melt was cooled and then dissolved under heating in pure water, and the content of the ruthenium component therein was measured by a ICP emission spectral analyzer. Also, the contents of the nickel component and the barium component were measured as follows. That is, sulfuric acid was added to a sample (catalyst), and the obtained mixture was heated. Further, appropriate amounts of hydrogen peroxide and nitric acid were added to the mixture, and the obtained solution was repeatedly heated until producing a transparent solution. The resultant transparent solution was cooled and then mixed with pure water, and the content of each of the nickel component and the barium component therein was measured by a ICP emission spectral analyzer.

Example 15

A 500 mL autoclave of an electromagnetic induction rotary agitation type was charged with 150 g (0.55 mol) of stearyl alcohol and 3 g of the catalyst (N) produced in Production Example 12 (2.0% by mass on the basis of the raw alcohol), and then 47 g (2.76 mol) of ammonia was charged into the autoclave and further 0.17 mol of hydrogen was introduced under pressure thereinto such that a whole pressure in the autoclave as measured at room temperature reached 2.3 MPaG. Next, the contents of the autoclave were heated to a reaction temperature of 220° C. while stirring (at 1000 rpm). The initial maximum pressure in the autoclave at 220° C. was 16 MPaG. While continuously supplying hydrogen into the autoclave such that a whole pressure therein was maintained at a constant pressure of 16 MPaG, the contents of the autoclave were reacted with each other. The resultant reaction product was filtered to remove the catalyst therefrom, and then subjected to gas chromatography to analyze a composition thereof. The results are shown in Table 3.

Example 16

The same procedure as in Example 15 was repeated except for using the catalyst (O) produced in Preparation Example 13 in place of the catalyst (N), and supplying an additional amount of hydrogen such that the initial maximum pressure as measured at a reaction temperature of 220° C. was maintained at a constant value shown in Table 3. The resultant reaction product was analyzed in the same manner as in Example 15. The results are shown in Table 3.

Examples 17 and 18

The same procedure as in Example 15 was repeated except for charging 6 g of each of the catalysts (P) and (Q) produced in Preparation Examples 14 and 15 (4% by mass on the basis of the raw alcohol), respectively, in place of the catalyst (N), and supplying an additional amount of hydrogen such that the initial maximum pressure as measured at a reaction temperature of 220° C. was maintained at a constant value shown in Table 3. The resultant reaction products were analyzed in the same manner as in Example 15. The results are shown in Table 3.

TABLE 3

| Catalyst | Initial maximum pressure (MPaG) | Reaction time (h) |
|---|---|---|
| Example 15 | N | 17 | 6.0 |
| Example 16 | O | 17 | 7.0 |
| Example 17 | P | 17 | 3.0 |
| Example 18 | Q | 16 | 3.0 |

| | Conversion of raw alcohol (%) | Selectivity to stearyl amine (%) | Products (%) | |
|---|---|---|---|---|
| | | | Distearyl amine | Others |
| Example 15 | 97.3 | 92.1 | 6.3 | 1.4 |
| Example 16 | 97.6 | 92.6 | 5.8 | 1.4 |
| Example 17 | 97.4 | 93.6 | 4.8 | 1.4 |
| Example 18 | 97.6 | 92.3 | 5.9 | 1.6 |

Example 19

The same procedure as in Example 15 was repeated except for using 150 g (0.81 mol) of lauryl alcohol in place of stearyl alcohol and using ammonia in an amount of 69 g (4.06 mol), thereby conducting the reaction for 9 h. The initial maximum pressure as measured at a reaction temperature of 220° C. was 21 MPaG. The resultant reaction product was analyzed in the same manner as in Example 15. As a result, it was confirmed that the conversion of the raw alcohol was 96.3%, the selectivity to lauryl amine was 90.9%, the amount of dilauryl amine produced is 8.2%, and the amount of the other by-products produced was 0.6%.

INDUSTRIAL APPLICABILITY

According to the process of the present invention, an aliphatic amine, in particular, an aliphatic primary amine can be produced from an aliphatic alcohol with a high catalytic activity and a high selectivity. The resultant aliphatic amines are important compounds in domestic and industrial application fields and are suitably used, for example, as raw materials for production of surfactants, fiber-treating agents, etc.

The invention claimed is:

1. A process for producing an aliphatic amine, comprising contacting a linear or branched, or cyclic aliphatic alcohol having 6 to 22 carbon atoms with ammonia and hydrogen in the presence of a catalyst that comprises, present on a carrier, (A) a ruthenium component produced by hydrolysis of a ruthenium compound.

2. The process according to claim 1, wherein the catalyst further comprises, present on the carrier, (B) at least one metal component selected from the group consisting of nickel, cobalt and tungsten, which is produced by hydrolysis of a compound of at least one metal selected from the group consisting of nickel, cobalt and tungsten.

3. The process according to claim 1, wherein the catalyst further comprises, present on the carrier, (B) at least one metal component selected from the group consisting of nickel and cobalt which is produced by hydrolysis of at least one of a nickel compound and a cobalt compound, and (C) at least one metal component selected from the group consisting of lanthanum, yttrium, magnesium and barium, which is produced by hydrolysis of at least one of a lanthanum compound, a yttrium compound, a magnesium compound and a barium compound.

4. The process according to claim 3, wherein a content of the at least one metal component (C) selected from the group consisting of lanthanum, yttrium, magnesium and barium in the catalyst is from 0.01 to 10% by mass in terms of the metal element on the basis of a total amount of the catalyst.

5. The process according to claim 1, wherein the carrier comprises at least one compound selected from the group consisting of a high molecular weight compound, a metal phosphate, and a porous oxide.

6. The process according to claim 1, wherein the carrier comprises a porous oxide.

7. The process according to claim 1, wherein the carrier comprises a porous oxide that is at least one oxide selected from the group consisting of alumina, zirconia, titania and an aluminosilicate diatomaceous earth, a hydrotalcite compound, an alkali earth metal oxide, and niobia.

8. The process according to claim 2, wherein a content of the component (B) in the catalyst is from 0.1 to 25% by mass in terms of the metal element on the basis of a total amount of the catalyst.

9. The process according to claim 1, wherein a content of the ruthenium component (A) in the catalyst is from 0.1 to 25% by mass in terms of metallic ruthenium on the basis of a total amount of the catalyst.

10. The process according to claim 1, wherein the catalyst is dried after said hydrolysis at a temperature of 140° C. or lower.

11. The process according to claim 1, wherein the catalyst is reduced after said hydrolysis in the presence of at least one reducing agent selected from the group consisting of formaldehyde, hydrazine and sodium borohydride.

12. The process according to claim 1, wherein said contacting is carried out at a temperature of 120 to 280° C.

13. The process according to claim 1, wherein said contacting is carried out under such a condition that a molar ratio of ammonia to the aliphatic alcohol (ammonia/aliphatic alcohol) is from 0.5 to 10.

14. The process according to claim 1, wherein the catalyst is present in an amount of 0.1 to 20% by mass on the basis of the aliphatic alcohol.

15. The process according to claim 1, wherein the aliphatic amine comprises an aliphatic primary amine.

16. The process according to claim 3, wherein a content of the component (B) in the catalyst is from 0.1 to 25% by mass in terms of the metal element on the basis of a total amount of the catalyst.

* * * * *